US009610397B2

(12) United States Patent
Cabiri et al.

(10) Patent No.: US 9,610,397 B2
(45) Date of Patent: Apr. 4, 2017

(54) SYSTEM AND METHOD TO DISTRIBUTE POWER TO BOTH AN INERTIAL DEVICE AND A VOLTAGE SENSITIVE DEVICE FROM A SINGLE CURRENT LIMITED POWER SOURCE

(71) Applicant: MEDIMOP Medical Projects Ltd., Ra'anana (IL)

(72) Inventors: Oz Cabiri, Macabim-Reut (IL); Gan Shmuel, Kiryat Ata (IL)

(73) Assignee: MEDIMOP MEDICAL PROJECTS LTD., Ra'anana (IL)

( * ) Notice: Subject to any disclaimer, the term of this patent is extended or adjusted under 35 U.S.C. 154(b) by 0 days.

(21) Appl. No.: 14/440,952

(22) PCT Filed: Nov. 20, 2012

(86) PCT No.: PCT/US2012/066036
§ 371 (c)(1),
(2) Date: May 6, 2015

(87) PCT Pub. No.: WO2014/081411
PCT Pub. Date: May 30, 2014

(65) Prior Publication Data
US 2015/0297824 A1  Oct. 22, 2015

(51) Int. Cl.
*H02P 7/29* (2016.01)
*A61M 5/14* (2006.01)
(Continued)

(52) U.S. Cl.
CPC ............ *A61M 5/14* (2013.01); *H02J 7/0063* (2013.01); *H02J 7/345* (2013.01); *H02P 7/29* (2013.01)

(58) Field of Classification Search
CPC ............ Y10T 307/696; Y10T 307/647; Y10T 137/86823; Y10T 307/615; Y10T 307/858;
(Continued)

(56) References Cited

U.S. PATENT DOCUMENTS 3,689,748 A * 9/1972 Bothne ................. G05B 15/02
137/625.41
4,126,132 A  11/1978 Portner et al.
(Continued)

FOREIGN PATENT DOCUMENTS

JP  S63287364 A  11/1988
JP  H10167593 A  6/1998

OTHER PUBLICATIONS

International Search Report dated Jul. 30, 2013 in International Application No. PCT/US2012/066036.
(Continued)

*Primary Examiner* — Paul Ip
(74) *Attorney, Agent, or Firm* — Panitch Schwarze Belisario & Nadel LLP

(57) ABSTRACT

A system may regulate voltage supplied from a power source to an integrated circuit and/or an inertial device. A minimal voltage may be maintained in the integrated circuit by temporarily cutting off current to the inertial device to supply surges of voltage to the controller. Optionally voltage may be smoothed between said surges for example by adding capacitance and/or a current restrictor.

15 Claims, 12 Drawing Sheets

(51) Int. Cl.
*H02J 7/34* (2006.01)
*H02J 7/00* (2006.01)

(58) Field of Classification Search
CPC .... G06F 1/1632; G06F 1/263; G06F 15/0216; G06F 1/1616; G06F 1/1677; G06F 1/1679; F02D 41/20; F02D 13/0253; F02D 2041/00
USPC .............................. 318/443, 466; 307/64, 66
See application file for complete search history.

(56) References Cited

U.S. PATENT DOCUMENTS

| | | | |
|---|---|---|---|
| 4,322,668 A * | 3/1982 | Trussler | H02P 7/347 318/432 |
| 4,497,036 A * | 1/1985 | Dunn | G06F 1/1616 361/679.09 |
| 4,645,326 A * | 2/1987 | Kiuchi | G03B 7/26 396/277 |
| 4,667,299 A * | 5/1987 | Dunn | G06F 1/1616 361/679.09 |
| 5,089,783 A * | 2/1992 | Kapsokavathis | G01N 33/2852 324/605 |
| 5,107,685 A * | 4/1992 | Kobayashi | G05D 23/19 318/807 |
| 5,430,636 A * | 7/1995 | Kachi | H02M 7/48 363/55 |
| 5,563,479 A * | 10/1996 | Suzuki | B60L 11/18 318/139 |
| 5,640,071 A | 6/1997 | Malaspina et al. | |
| 5,661,372 A * | 8/1997 | Ishimaru | H05B 41/34 315/241 P |
| 5,683,367 A | 11/1997 | Jordan et al. | |
| 5,839,537 A * | 11/1998 | Nishino | B62D 5/0466 180/443 |
| 5,884,237 A * | 3/1999 | Kanki | G05B 19/4062 318/466 |
| 6,081,098 A * | 6/2000 | Bertness | H02J 7/0077 320/134 |
| 6,139,399 A * | 10/2000 | DeAngelis | A63H 30/04 446/456 |
| 6,270,478 B1 | 8/2001 | Mernøe | |
| 6,331,762 B1 * | 12/2001 | Bertness | G01R 31/3627 320/134 |
| 6,910,138 B2 * | 6/2005 | Hayashi | G06F 1/1632 713/300 |
| 6,943,531 B2 * | 9/2005 | Fukaya | F01L 13/085 307/46 |
| 7,054,737 B2 * | 5/2006 | Degner | F01L 9/04 123/198 F |
| 7,064,454 B2 * | 6/2006 | Fukaya | F02B 63/04 290/1 A |
| 7,075,311 B1 * | 7/2006 | Oshiro | G01R 31/1272 324/557 |
| 7,124,310 B2 * | 10/2006 | Hayashi | G06F 1/1632 307/80 |
| 7,126,341 B2 * | 10/2006 | Bertness | G01R 31/3624 324/426 |
| 7,127,288 B2 | 10/2006 | Sturman et al. | |
| 7,292,462 B2 * | 11/2007 | Watanabe | H02M 3/158 307/110 |
| 7,579,716 B2 * | 8/2009 | Sato | G03G 15/5004 219/216 |
| 7,612,542 B2 * | 11/2009 | Eguchi | H02M 3/156 323/222 |
| 7,642,787 B2 * | 1/2010 | Bertness | G01R 31/3624 324/426 |
| 7,690,456 B2 * | 4/2010 | Deng | B60K 6/26 180/65.265 |
| 7,705,602 B2 * | 4/2010 | Bertness | G01R 31/007 320/104 |
| 8,008,892 B2 * | 8/2011 | Kikuchi | G03G 15/0283 320/127 |
| 8,493,022 B2 * | 7/2013 | Bertness | G01R 31/007 320/104 |
| 2002/0026594 A1 * | 2/2002 | Hayashi | G06F 1/1632 713/300 |
| 2003/0038637 A1 * | 2/2003 | Bertness | G01R 31/3624 324/426 |
| 2004/0008009 A1 * | 1/2004 | Fukaya | F01L 13/085 322/44 |
| 2005/0038388 A1 | 2/2005 | Hommann et al. | |
| 2005/0174098 A1 * | 8/2005 | Watanabe | H02M 3/158 323/282 |
| 2005/0189923 A1 * | 9/2005 | Ohishi | H02J 7/022 320/138 |
| 2005/0201050 A1 * | 9/2005 | Hayashi | G06F 1/1632 361/601 |
| 2005/0209768 A1 * | 9/2005 | Degner | F01L 9/04 701/103 |
| 2007/0203528 A1 * | 8/2007 | Vernon | A61N 1/08 607/34 |
| 2007/0212103 A1 * | 9/2007 | Kikuchi | G03G 15/0283 399/88 |
| 2007/0274736 A1 * | 11/2007 | Sato | G03G 15/5004 399/88 |
| 2007/0279011 A1 * | 12/2007 | Jones | H01G 9/14 320/167 |
| 2008/0068870 A1 * | 3/2008 | Eguchi | H02M 3/156 363/37 |
| 2008/0191556 A1 * | 8/2008 | Hong | H02J 9/061 307/64 |
| 2008/0259666 A1 * | 10/2008 | Eguchi | H02J 7/34 363/131 |
| 2008/0315829 A1 * | 12/2008 | Jones | H02J 7/345 320/103 |
| 2009/0054832 A1 | 2/2009 | Sugimoto et al. | |
| 2010/0019705 A1 * | 1/2010 | Kimura | H02M 7/4807 318/400.3 |
| 2010/0121277 A1 | 5/2010 | Fehr et al. | |
| 2010/0253140 A1 * | 10/2010 | Yamashita | B62D 5/0457 307/9.1 |
| 2010/0262404 A1 * | 10/2010 | Bertness | G01R 31/007 702/183 |
| 2011/0031805 A1 * | 2/2011 | Yamashita | B62D 5/046 307/9.1 |
| 2011/0057510 A1 * | 3/2011 | Yamashita | B60L 1/003 307/10.1 |
| 2011/0098887 A1 * | 4/2011 | Fujimoto | B62D 5/0481 701/41 |
| 2011/0264326 A1 * | 10/2011 | Iwasaki | B62D 5/046 701/41 |
| 2011/0272205 A1 * | 11/2011 | Fujimoto | B62D 5/046 180/446 |
| 2011/0273148 A1 * | 11/2011 | Ueno | B60L 11/123 322/28 |
| 2012/0192837 A1 * | 8/2012 | Kitamura | F02D 41/20 123/480 |
| 2012/0227729 A1 * | 9/2012 | Lundahl | F24J 2/38 126/601 |
| 2013/0002045 A1 * | 1/2013 | Hassan-Ali | H01L 31/02021 307/130 |

OTHER PUBLICATIONS

Adler et al, "Pulse Width Modulation", Electronics in Meccano, No. 6, Published Jan. 2000, retrieved from http://www.http://www.eleinmec.com/article.asp?28 on Jun. 11, 2012.

Int'l Preliminary Report on Patentability issued Jun. 4, 2015 in Int'l Application No. PCT/US2012/066036.

* cited by examiner

SYSTEM AND METHOD TO DISTRIBUTE POWER TO BOTH AN INERTIAL DEVICE AND A VOLTAGE SENSITIVE DEVICE FROM A SINGLE CURRENT LIMITED POWER SOURCE

CROSS-REFERENCE TO RELATED APPLICATION

This application is a section 371 of International Application No. PCT/US2012/066036, filed Nov. 20, 2012, which was published in the English language on May 30, 2014 under International Publication No. WO 2014/081411, the disclosure of which are incorporated herein by reference.

BACKGROUND OF THE INVENTION

The present invention, in some embodiments thereof, relates to a power distribution system and, more particularly, but not exclusively, to a system and method to supply simultaneously from a single power source a desired voltage to a CPU and a power to an inertial device, for example to a controller and motor of an infusion device.

Portable devices often require powering of various components from a single power supply. Under some conditions the power output of the power supply may not simultaneously fill the needs of all of the components. A large number of devices exist for power regulation to solve this problem. In particular, portable infusion devices may have need for strictly controlled and reliable pumping of medicine using a small disposable device.

US publication no. 2005/0038388 to Hommann et al. discloses an injection device including a capacitor as an energy accumulator for providing energy for performing an injection. In some embodiments, a voltage regulator, in particular a DCDC converter such as one of those known in the electrical art, is preferably connected to the capacitor, such that a substantially constant DC voltage for operating the injection device, for example an electric motor associated with the injection device, can be obtained from the variable DC voltage on the capacitor. Buck converters and boost converters are known, using which a DC voltage can be obtained above or below the input voltage. A buck-boost converter or an inverting circuit regulator can equally be used.

U.S. Pat. No. 4,126,132 to Portner and Jassawalla discloses an intravenous and ultra arterial delivery system having a disposable cassette actuated by a pump and control electronics for providing positive but variable delivery rates. The electronics has low power consumption so as to be suitable for battery operation, such as by way of rechargeable batteries.

US publication no. US 2010/0121277 to Fehr et al. discloses a medical infusion system with pulse width modulation and a safety circuit and a method thereof. Embodiments of the system include a switching device and a pump motor, wherein the pump motor and the switching device are connected in series and constitute a power supply circuit to be connected to a power supply. Embodiments of the system further includes a control signal generator configured to generate a control signal e.g. PWM, and which is connected to input of the safety circuit. Output of the safety circuit is connected to a control input of the switching device such that the pump motor will not operate if there is no control signal applied to the input of the safety circuit.

US Publication no. US 2009/0054832 to Sugimoto et al. discloses an administration apparatus for medical use which is driven by an electric driving source to perform administration of a drug. Low-speed operation during air releasing operation is performed by PWM (Pulse Width Modulation) control.

Additional background art includes U.S. Pat. No. 5,683,367 to Jordan et al. and U.S. Pat. No. 6,270,478 to Mern.

BRIEF SUMMARY OF THE INVENTION

According to an aspect of some embodiments of the present invention there is provided a method to increase a voltage potential available to an integrated circuit device sharing a battery power source with an actuator. The method may include producing transient high voltage surges in the battery output by repeatedly cutting off power to the actuator. The method may further include storing energy during the surges and releasing the stored energy to maintain an input voltage to the integrated circuit above the threshold voltage when a voltage output of the battery falls below a threshold voltage.

According to some embodiments of the invention, the cutting off of power may be controlled by the integrated circuit.

According to some embodiments of the invention, the method may further include preventing leakage of the released energy away from the integrated circuit.

According to some embodiments of the invention, the repeatedly cutting may have a period of between 5 and 50 milli-seconds.

According to some embodiments of the invention, the repeatedly cutting may have a duty cycle of between 50% and 95%.

According to some embodiments of the invention, the method may further include pumping a medicine with the actuator and controlling a rate of the pumping with the integrated circuit.

According to some embodiments of the invention, the controlling may be adjusted for the maintaining the voltage threshold to the integrated circuit. For example the adjusting may account for an output limitation of the battery and a limit of the storage.

According to some embodiments of the invention, the controlling may be by pulse density modulation.

According to some embodiments of the invention, the pulse density modulation may have a pulse width of between 50 and 500 milli-seconds.

According to some embodiments of the invention, the pulse density modulation may have a duty cycle of between 2% and 20%.

According to some embodiments of the invention, the method may further include testing a voltage input to the integrated circuit and adjusting the cutting off of power to the actuator according to a result of the testing in order to maintain a threshold voltage to the integrated circuit.

According to some embodiments of the invention, the adjusting of the cutting off of power may include lengthening a period of the cutting off in response to a low voltage measurement, shortening a period between the cut off periods in response to a low voltage measurement and/or reducing a duty cycle of the actuator in response to a low voltage measurement.

According to some embodiments of the invention, the method may further include storing performance data in a non-volatile memory when there is low voltage input to the integrated circuit. The method may further include restarting the system after a shut down and checking the performance data after the restarting. The cutting off of power to the actuator upon the restart may be adjusted according to the performance data to prevent further failure.

According to some embodiments of the invention, the performance data may include a voltage output of the battery, a voltage input of the integrated circuit and/or a current input to the actuator.

According to some embodiments of the invention, the adjusting may include lengthening a period of the cutting off in response to a low value of the voltage input measurement, shortening a period between the cut off periods in response to a low value of the voltage input measurement, reducing a duty cycle of the actuator in response to a low value of the voltage input measurement, lengthening a period of the cutting off in response to a low value of the voltage output measurement, shortening a period between the cut off periods in response to a low value of the voltage output measurement and/or reducing a duty cycle of the actuator in response to a low value of the voltage output measurement.

According to an aspect of some embodiments of the present invention there is provided a system to distribute power among a plurality of components of a portable device. The system may include a first circuit powering an electrical actuator and a second circuit powering an integrated circuit. The system may also include a power distributor connected to a battery. The power distributer may be configured to supply to the first circuit, higher current pulses of power from the battery having sufficient energy to power the actuator, and to at least partially cut off power to the first circuit between the pulses to produce voltage surges having sufficient energy to power the integrated circuit at a higher voltage potential than the higher current pulses.

According to some embodiments of the invention, the system may further include an energy storage device connected to the second circuit. The energy storage device may be configured to store energy at a high voltage during the voltage surges, and to release the stored energy to the integrated circuit between the voltage surges.

According to some embodiments of the invention, the actuator may include a medicine pump and the integrated circuit may include a controller for the pump.

According to some embodiments of the invention, the distributer may be controlled by the integrated circuit.

According to some embodiments of the invention, the system may further include a sensor to sense a voltage input to the integrated circuit. The integrated circuit may be configured to adjust the distributer in response to an output of the sensor to preserve a threshold voltage to the integrated circuit.

According to some embodiments of the invention, the system may further include a restrictor to prevent power leakage from the integrated circuit to the actuator.

According to some embodiments of the invention, the restrictor may include a diode and/or an electronic switch.

According to some embodiments of the invention, the integrated circuit may be configured to adjust the distributer in response to an aging of the battery.

According to some embodiments of the invention, the actuator may have an inertia to keep running over an inertial period. The distributer may be configured to keep a length of a cut off period between the high current pulses less than a length of the inertial period.

According to some embodiments of the invention, system may further include a voltage sensor configured to measure an input voltage to the integrated circuit. The integrated circuit may be configured to receive output from the sensor and to adjust the distributor in response to the output of the sensor to maintain the input voltage greater than a threshold value.

According to some embodiments of the invention, the adjusting may include lengthening a period of the cutting off in response to a low value of the voltage input measurement, shortening a period between the cut off periods in response to a low value of the voltage input measurement, reducing a duty cycle of the actuator in response to a low value of the voltage input measurement, lengthening a period of the cutting off in response to a low value of the voltage output measurement, shortening a period between the cut off periods in response to a low value of the voltage output measurement, and/or reducing a duty cycle of the actuator in response to a low value of the voltage output measurement.

According to some embodiments of the invention, the system may further include a sensor configured to measure a voltage output of the battery and/or a current input of the actuator. Operation of the distributor may be adjusted according to an output of the sensor.

According to some embodiments of the invention, the system may further include a non-volatile memory. The memory may be configured to store a performance parameter. The integrated circuit may be configured to read the non-volatile memory upon a start up of the system and to adjust an operation of the distributor in response to the performance parameter.

According to some embodiments of the invention, the performance parameter may include a voltage output of the battery, a voltage input of the integrated circuit, a current input of the actuator, a number of rotations of a motor and/or a preprogrammed parameter.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
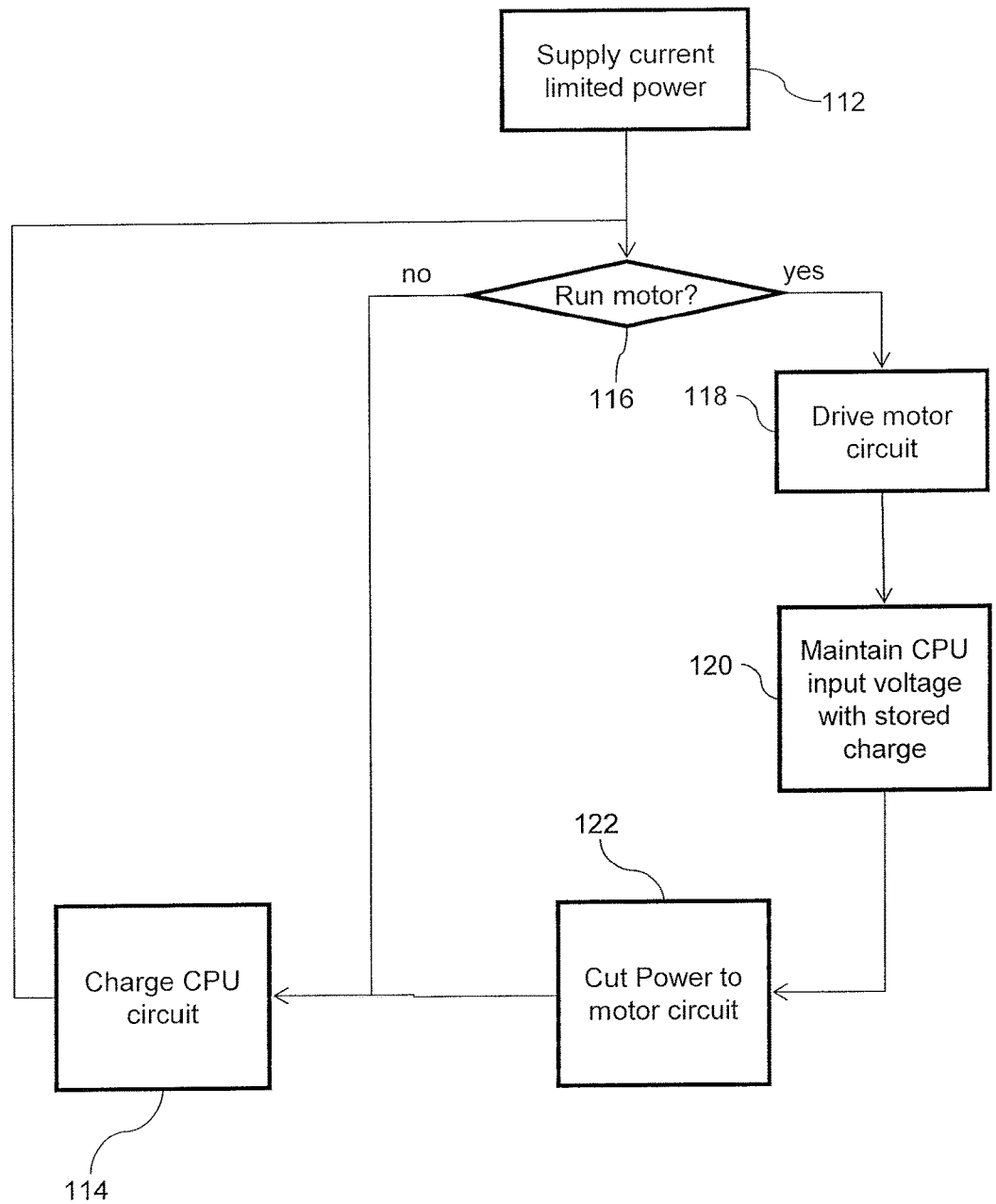
FIG. 1 is a flow chart illustrating an exemplary embodiment of a method of providing power to multiple devices.

The present invention, in some embodiments thereof, relates to a power distribution system and, more particularly, but not exclusively, to a system and method to supply simultaneously from a single power source a desired voltage to a CPU and a power to an inertial device, for example to a controller and motor of an infusion device.

Overview

It is sometime desirable to power two devices from a single power source. In some cases, the output of the power source may be limited, for example, the output voltage of a battery may be dependent on the current drawn.

In some cases, the power output function of the power supply may not be suited to supply directly the simultaneous power requirements of different components. For example, in some embodiments, it may be desired to simultaneously supply high current to an inertial device and high voltage to a processor. Some embodiments of a battery may be capable of supplying a high current at a low voltage (that may optionally be sufficient for the inertial device) or a low current at a high voltage (that may optionally be sufficient for the processor). Nevertheless, the battery may be limited in its ability to directly supply high current at a high voltage sufficient time to both components over a long time period.

In some embodiments of the current invention the output of a power supply may optionally be distributed in time to supply the various components. Optionally, a high power component (for example an actuator including for example a DC motor) may be driven with pulses of power. In some embodiments, a component requiring high voltage (for example an integrated circuit including for example a CPU) may be powered by high voltage surges that may occur while power to the motor is cut off between the pulses.

Optionally, power interruptions may be short enough for the devices to continue functioning (for example the motor may continue to spin due to inertia between pulses). Optionally, an energy storage device (for example a capacitor) may be supplied to smooth out interruptions (for example to stabilize voltage to a CPU between voltage surges).

In some embodiments, the current distribution may be tuned to preserve a voltage input to the integrated circuit and not necessarily to achieve a particular speed or output or performance of the motor. For example the distribution parameters (frequency, duty cycle etc.) may be fixed (for example to achieve a reliable minimal CPU input voltage under a variety of conditions). Alternatively or additionally, the distribution parameters may be adjusted according to the CPU input voltage requirements regardless of the motor performance (within limits). Alternatively or additionally, the distribution parameters may be dynamically adjusted while the system is running according to the CPU input voltage requirements with some limitations based on minimal standards of the motor performance.

In various embodiments, pulses of power to the motor may last from example from 5-50 msec. The pulses may supply the motor with a high current of for example from 100-400 mA, for example at start up. The breaks between pulses may be, for example, between 1-15 msec. Optionally, a CPU reset threshold may fall between 1.5 and 3.5 V. Optionally a CPU may draw between 0.1 and 1.0 mA. Optionally, a motor may draw, for example, current ranging between 30 and 200 mA while running.

In some embodiments, the pulses may be simple and/or fixed. For example the pulse length and/or the length of time between pulses and/or the duty cycle of the system may be fixed. Additionally or alternatively the oscillator may be programmable or adjustable prior to operation to compensate for conditions of the system (for example aging of a battery or a high load on a motor) or operating conditions (for example short term or long term operation). Additionally or alternatively, the oscillator may be dynamically adjustable during operation.

In some embodiments, the current invention may be capable of very high efficiency (efficiency here is defined as power input to the active devices [e.g. the motor and the CPU] divided by the power output of the battery). For example, while the motor is stopped, the system may have an efficient greater the 98%.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

An Exemplary Method of Powering Two Devices

FIG. 1 illustrates an exemplary embodiment of method supplying 112 power to two devices with a single, current limited power source, for example a battery. Optionally, power is distributed in time. For example during a first time period the battery drives a high current low voltage device. Optionally, during a second period, power is cut off to the high current device. During the cut off period, in some embodiments, the voltage output of the battery may surge. The high voltage battery output during the surge period may be used for example to power a second device, for example a CPU requiring high voltage and low current. In some embodiments, during the cut off period, power to the high current device may be only partially cut off.

In the exemplary embodiment of FIG. 1, a motor and a CPU both receive power from the battery. In the exemplary embodiment, during a 20 msec (milli-second) time period while the motor is running 116, the motor is driven 118 by a high current pulse for 15 msec. In some embodiments, while the power source is driving 118 the motor, the voltage output of the power source may fall below the required input voltage of the CPU. Optionally, the CPU circuit may include power storage (for example capacitance) and the CPU voltage may be maintained 120 during the motor pulse by power draining from the capacitance of the CPU circuit.

Optionally, for the remaining 5 msec of the period, power to the motor is cut 122. In the example, when power to the motor is cut 122, the only drain on the power source is charging 114 a low current CPU circuit. With a low current drain on the power source, the power source may optionally provide a high voltage potential output. In some embodiments, while the current output from the battery is low, then the CPU circuit is charged 114 at a high voltage potential.

A System for Powering Two Devices

Figure 2:
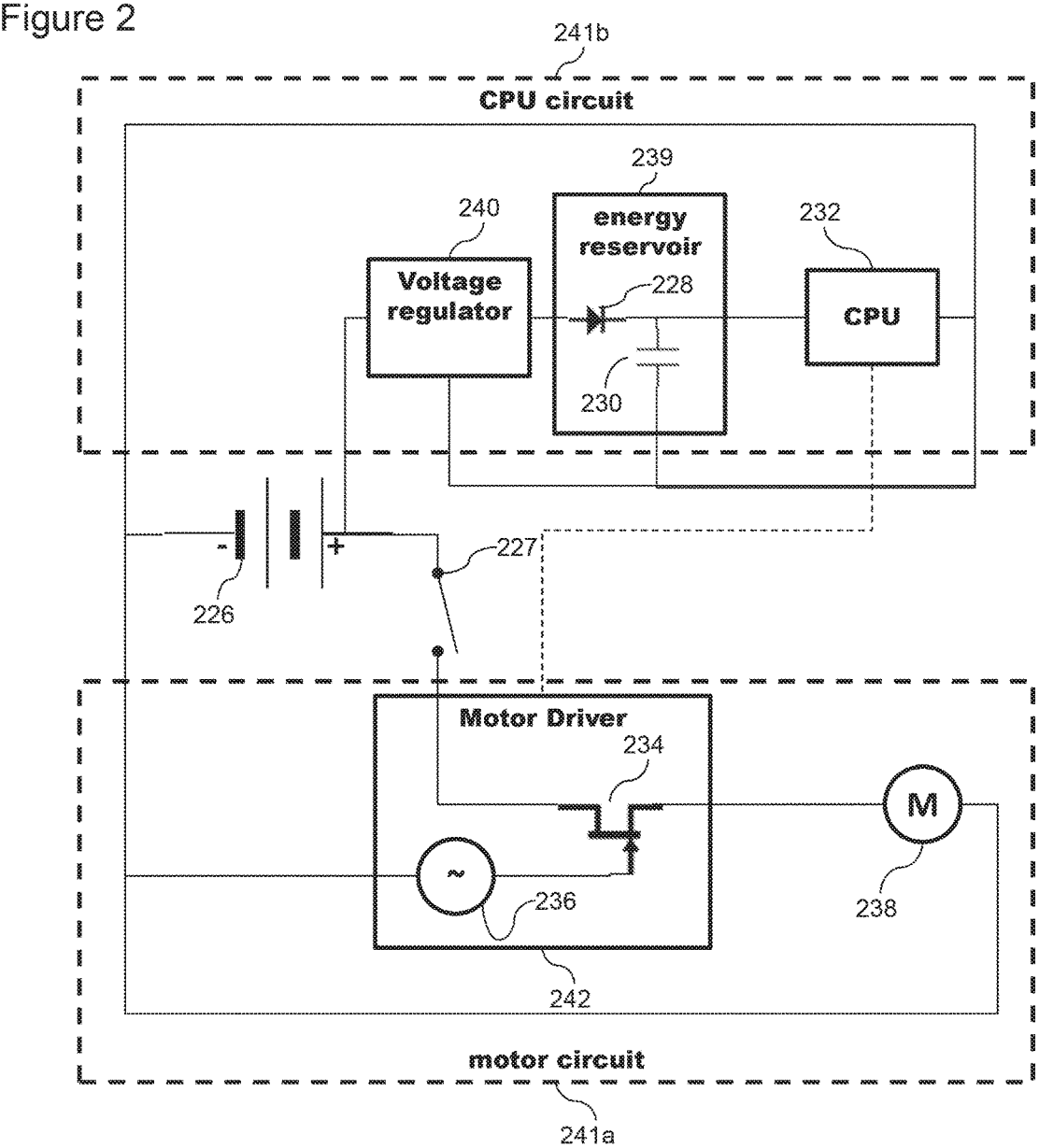
FIG. 2 is a circuit diagram of an exemplary embodiment of a system to provide power to two devices.

FIG. 2 illustrates an exemplary embodiment of a system for powering multiple devices. In the exemplary embodiment, a CPU 232 and a motor 238 receive power from batteries 226. Optionally, a motor circuit 241*a* includes a motor driver 242 which distributes current to motor 238 into pulses. During the pulses, the high load on batteries 226 may reduce the voltage output of batteries. Between pulses, the voltage output may surge upward. Optionally, a CPU powering circuit 241*b* may include a voltage regulator 240 to protect CPU 232 from high voltage surges and/or an energy reservoir 239 to smooth voltage between the surges, preserving a relatively constant high voltage power to the CPU.

In the exemplary embodiment of FIG. 2, a power source may include for example a set of three Silver Oxide (Ag2O) batteries 226. In some embodiments, three fresh Ag2O batteries 226 may have a reliable continuous output of 4.5 V at current of up to 12 mA for up to 100 hours.

In the exemplary embodiment of FIG. 2 it may be desired to use batteries 226 to simultaneously power motor 238 drawing 150 mA at start up and 50 mA while running. In the exemplary embodiment of FIG. 2, a CPU may have a current requirement of 0.3 mA and a voltage reset threshold of 2.4 V.

In some embodiments, when motor 238 is switched on (for example using switch 227) and runs continuously, the high current load of motor 238 may cause the voltage output of battery 226 to drop below the reset threshold of CPU 232.

In the exemplary embodiment of FIG. 2, motor driver 242 may include an oscillator 236. Optionally motor driver 242 may include a switch, for example a FET 234. In the example of FIG. 2, oscillator 236 may send a fixed pattern signal to FET 234 for alternatively driving pulses of power to motor 238 and cutting off power to motor 238. In the example of FIG. 2, pulses of power may last for 15 msec and subsequently power to motor 238 may be cut off for 5 msec. During the 15 msec driving period, the voltage output of batteries 226 may be reduced to between 1.5 and 2.5 V. During the 5 msec cut off period, the voltage output of batteries 226 may rise back to between 4.0 and 4.5 V.

In the embodiment of FIG. 2, energy reservoir 239 includes a capacitor 230 and a restrictor 228. Optionally, during a voltage surge (for example between pulses), capacitor 230 may store power. When voltage declines (for example when motor 238 is drawing a pulse of power from battery 226), capacitor 230 may optionally feed the stored power to CPU 232. In the embodiment of FIG. 2, capacitor 230 may be for example a 100 μF capacitor. In some embodiments, the capacitance may range, for example, between 20 and 300 μF. Optionally, restrictor 228 may include a diode. Restrictor 228 may prevent leaking of charge from capacitor 230 to batteries 226 or to motor circuit 241*a*.

In some embodiments, the combination of motor driver 242 and energy reservoir 239 may temporarily (for example for a time period ranging between 5 msec to 50 msec) maintain a voltage input to CPU above the voltage of the power source of the CPU. This may optionally be done without a boost converter. Optionally, the voltage to the CPU may be maintained above a threshold value even when the power source output (for example output of batteries 226) temporarily and/or cyclically falls below the threshold.

In some embodiments, active cutting 122 of power occurs when the motor is running. Optionally, cutting may not occur when the motor is not running (for example during a sleep period wherein the CPU is running, but not the motor). In some embodiments, this may mean that the system described herein requires very little power during breaks when the motor is not running.

Voltage Vs. Time at the IC and at the Motor

Figure 3A:
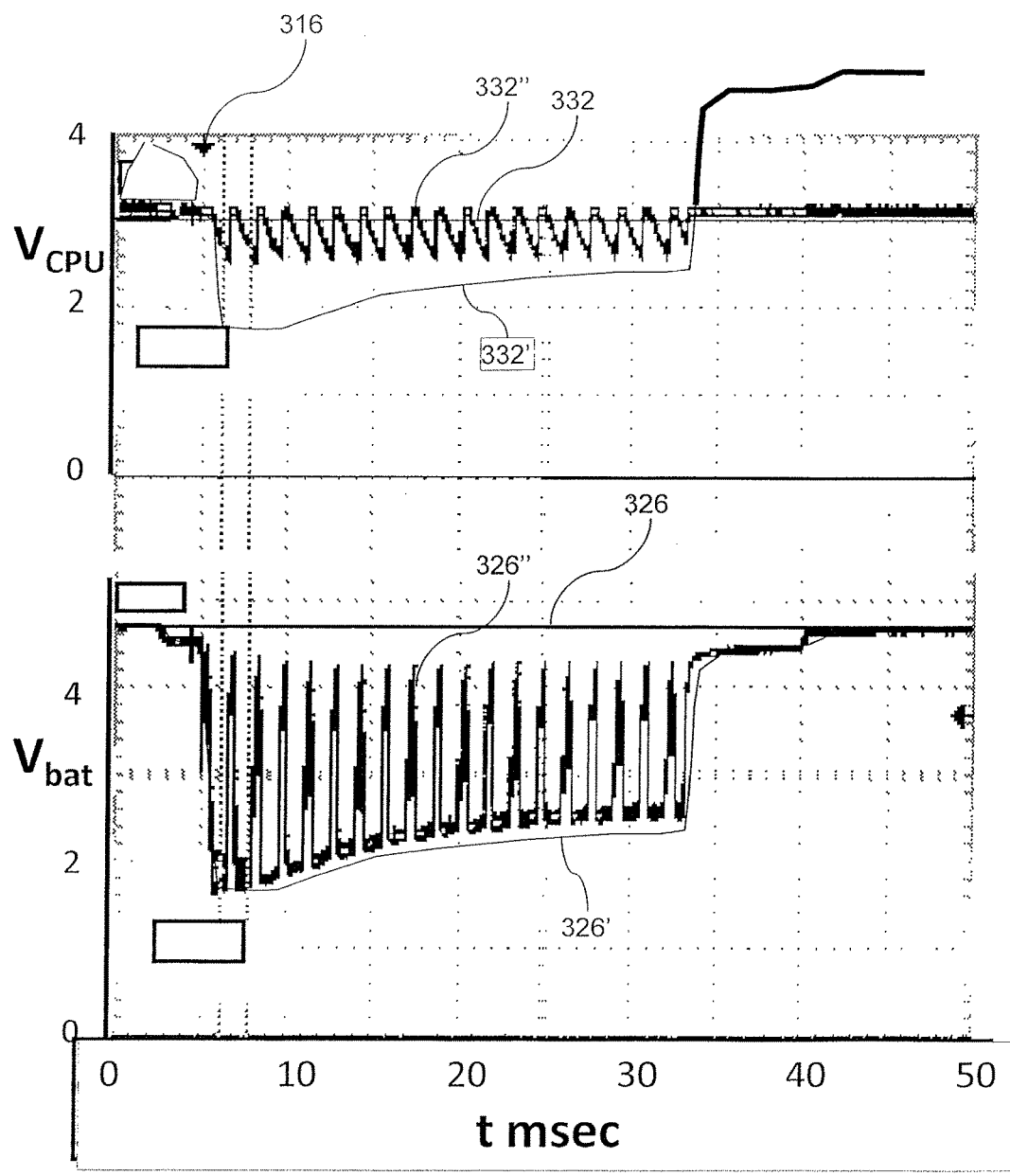
FIG. 3A is a graph showing experimental results of voltage over time to two devices powered by an exemplary embodiment of a method of providing power to multiple devices.

FIG. 3A includes graphs of experimental results compared to hypothetical curve of Voltage and/or Current vs. time across an inertial device (for example motor 238) and across an IC (for example CPU 232).

Various embodiments and aspects of the present invention as delineated herein and as claimed in the claims section below find experimental support in the example of FIG. 3A.

Reference is now made to the examples of FIG. 3A, which together with the descriptions herein illustrate some embodiments of the invention in a non limiting fashion.

Figure 7:
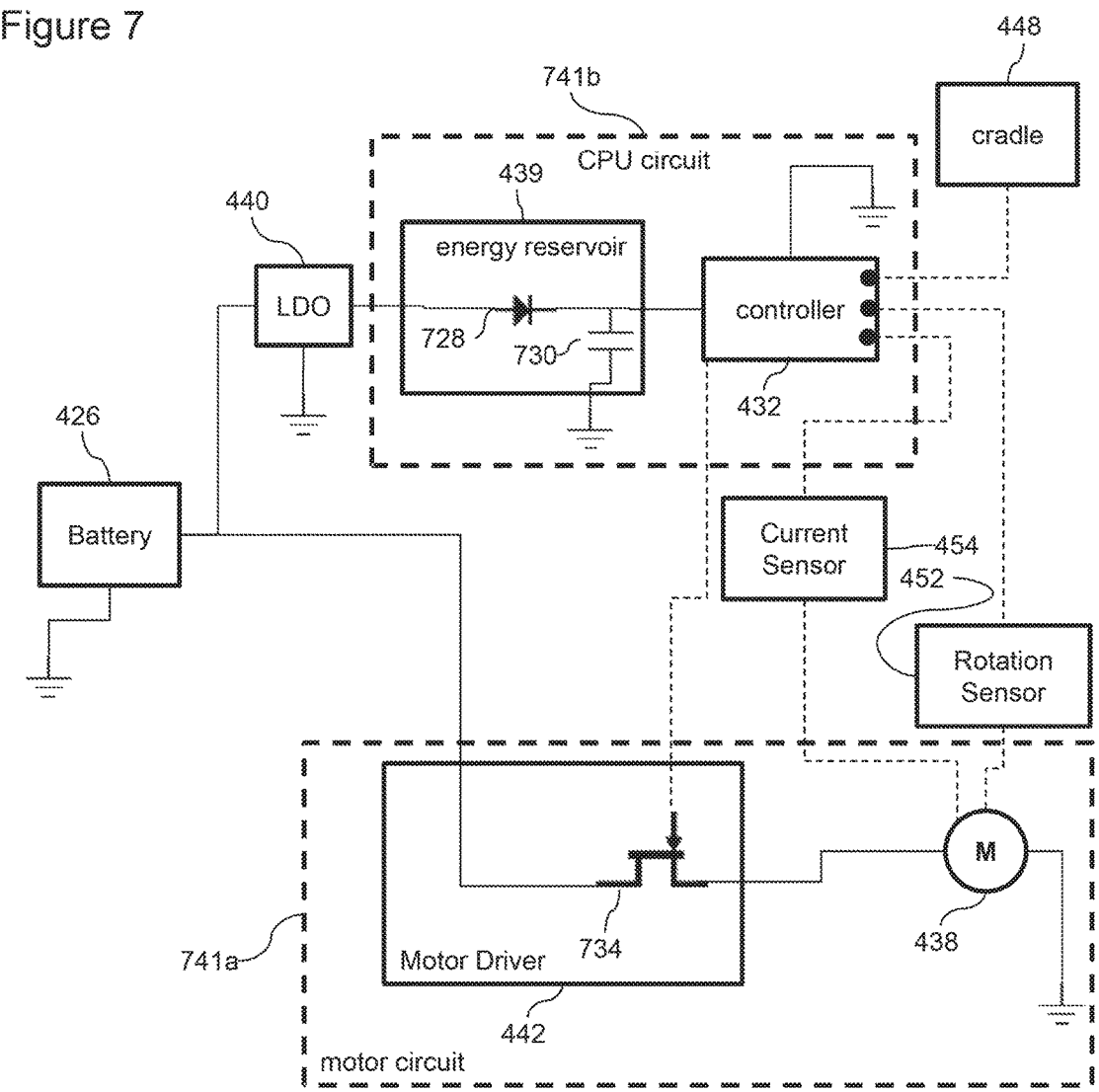
FIG. 7 is a detailed circuit diagram of an exemplary embodiment of a system to provide power to two devices.

Some details of the exemplary experimental circuit used in FIG. 3 are shown in FIG. 7. The simulated portions of FIG. 3A illustrate that, for the experimental setup, when the motor is connected directly to the battery, the output battery voltage 326' quickly drops to less than the reset threshold (2.4 V) of the IC. The experimental results illustrated in FIG. 3 show that with protection of a distributing motor driver (in the example driver 442 [see FIG. 7]), a voltage regulator, (in the example regulator 440440), and an energy reservoir (in the example reservoir 439) the IC input voltage 332" is maintained above the CPU reset voltage.

In FIG. 3A the lower graph shows the battery output voltage. A simulated unloaded output voltage 326 of 4.5 V of three Ag2O batteries 226 is shown. A second simulated curve shows the output battery voltage 326' when connected directly to the motor. Very soon after the motor is turned on at t=5 msec 316, output battery voltage 326' drops well below 2.4 V. If a CPU having a reset threshold of 2.4 V were connected to the battery with no protection, it could reset. An example of the effect of distributing motor input voltage (for example using driver 442) is seen in the experimentally measured battery voltage curve 326". It is seen that when the motor is activated the voltage 326" is quickly reduced to less than 2.4 V. Nevertheless, during cut off periods, when the motor is not drawing current, the voltage rises back to above 4 V.

In FIG. 3A, the upper graph shows the CPU input voltage. Simulated, voltage curve 332 shows the hypothetical voltage for a CPU connected to an unloaded battery and a low dropout voltage regulator (for example, regulator 440 which may include, for example, a LP2980 voltage regulator available from Texas Instruments, Post Office Box 655303, Dallas, Tex. 75265). Low dropout regulator 440 maintains the CPU voltage at 3.0 V as long as the battery output voltage is greater than 3.0 V. When the battery output falls below 3.0 V, low dropout regulator 440 may not boost the voltage. This can be seen in the hypothetical CPU input voltage 332' which is indicative of the CPU voltage that would result without redistributing battery output voltage 326'. In some embodiments, the CPU may reset when to voltage passes below a threshold (for example 2.0 V), resetting the CPU may in some embodiments lead to the entire system shutting down. In such an embodiment, the curves 332' and 326' may be replaced by, for example a line that starts like line 332 and goes down to 2.0V (for example as approximately 8 seconds) and then shuts down; after shutdown, voltage may optionally return to baseline.

An experimentally measured CPU input voltage 332'' illustrates the effect of adding a distributing motor drive (for example motor driver 442; see FIG. 7) and simple capacitance energy reservoir (for example energy reservoir 439 see FIG. 7) to the system. Note that in the example, even though the power source (for example battery output voltage 326'') drops transiently to less than 2 V, energy reservoir 439 maintains CPU input voltage 332'' above the 2.4 V cutoff voltage threshold.

Multi-Scale Time Considerations

Figure 3B:
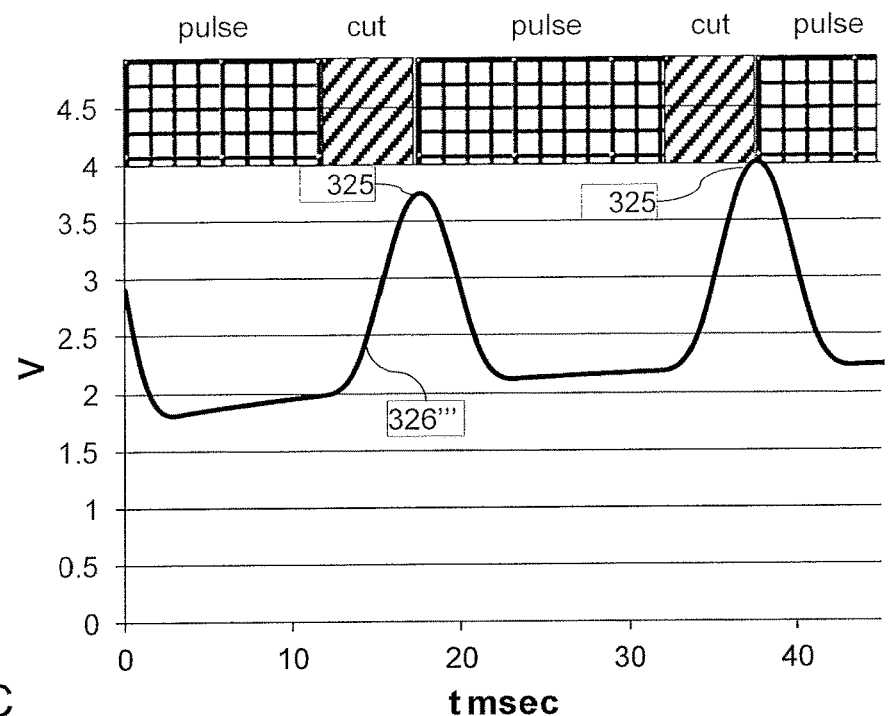
FIG. 3B is an expanded scale schematic diagram showing details of voltage over time to two devices powered by an exemplary embodiment of a method of providing power to multiple devices.
Figure 3C:
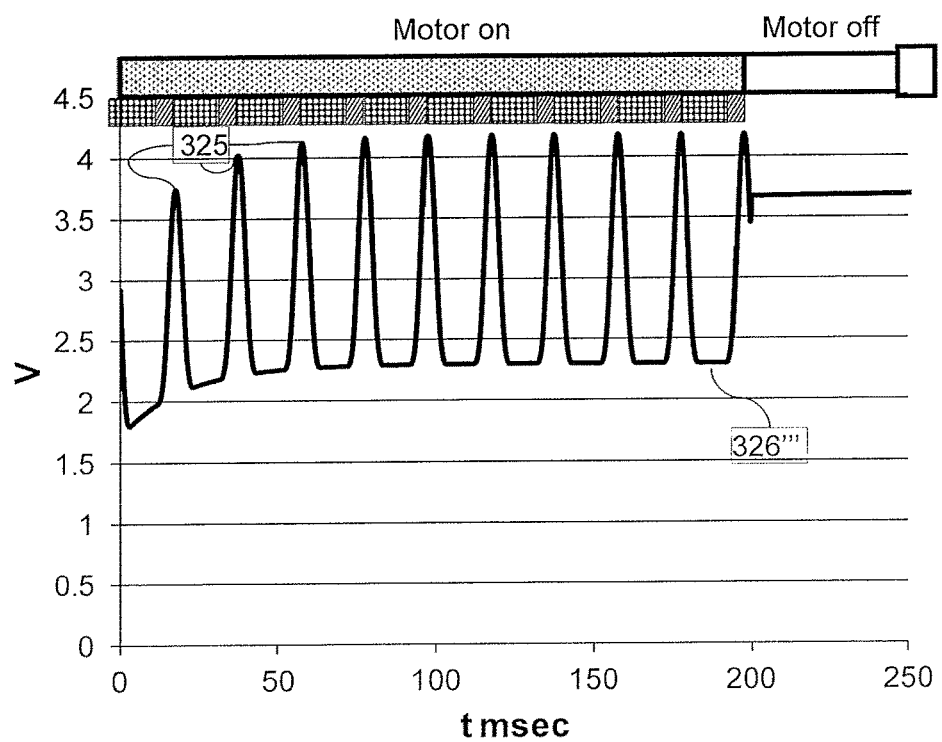
FIG. 3C is a schematic diagram showing details of voltage over time to two devices powered by an exemplary embodiment of a method of providing power to multiple devices.
Figure 3D:
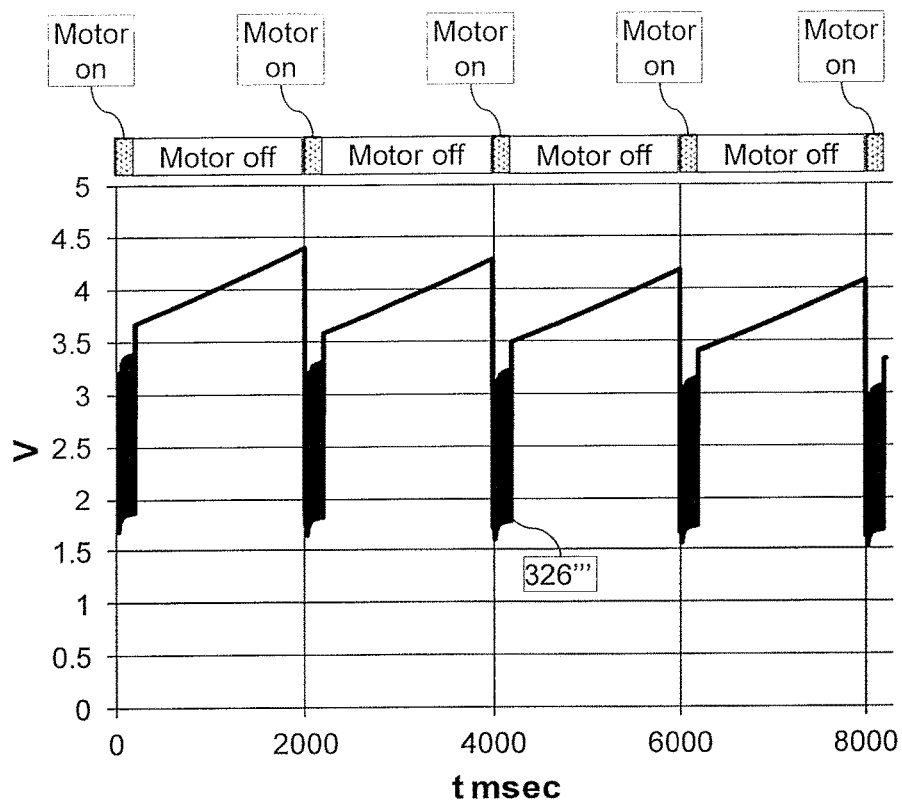
FIG. 3D is a large scale schematic diagram showing a few cycles of voltage over time to two devices powered by an exemplary embodiment of a method of providing power to multiple devices.

FIGS. 3B, 3C and 3D are graphs of simulated voltage 326'' data at the battery illustrating some exemplary changes in voltage at a few different time scales.

FIG. 3B illustrates an exemplary simulated voltage 326'' over time for a battery on a time scale of the time slicing (for example over 50 msec). For example, two 15 msec pulses are shown and two 5 msec motor cut off periods are shown. During each motor cut off period there is a voltage surge 325.

FIG. 3C is a graph illustrated an exemplary motor-on period of 200 msec. Optionally, during the motor-on period, the power is sliced between a motor and an integrated circuit. In the example of FIG. 3C, during the 200 msec motor-on period, there are 10 slicing periods, each slicing period having for example a 15 msec pulse of power to the motor and a 5 msec period where power to the motor is cut. Optionally, during the 10 power cutting periods, there occur 10 voltage peaks 325. Following the motor-on period there is a motor-off period. The duty cycle of the slicing may be defined as the length of the pulses during an on period divided by the length of the on period. For example in the illustration 10 pulses of 15 msec each over a 200 msec on period give a duty cycle of 10*15/200=0.75 or 75%. Optionally, the length of the pulses and/or the cutting off periods need not be fixed. For example, the length of the pulses and/or the cutting off periods may vary during and/or between on periods.

FIG. 3D is a graph illustrating an exemplary embodiment of pulse density modulation (PDM) wherein on 200 msec periods are spread among 1800 msec sleep periods when the motor is off. In FIG. 3D there is illustrated that is some cases there may be a slow degradation of the battery voltage. Slow degradation may be caused, for example, by chemical fatigue of the battery, for example due to slow diffusion of ions across a semi-permeable membrane. In the example of FIG. 3D, the battery partially recovers during the off periods of the PDM, but the off periods are not long enough for full regeneration of the battery.

Figure 3E:
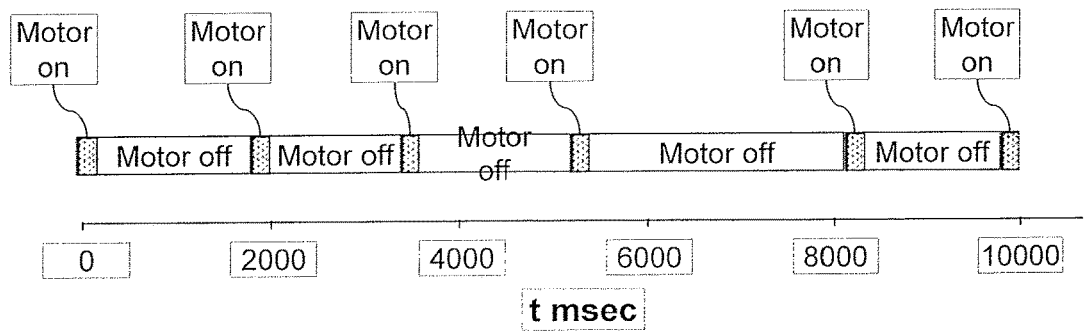
FIG. 3E is a diagram on off cycles for an exemplary embodiment of variable length power cycles.

FIG. 3E is a schematic illustration of an exemplary embodiment of PDM, wherein fixed time length motor-on periods are spread among varying time length sleep periods (when the motor is off). Optionally, the amount of work done by the motor may be controlled by adjusting the length of the sleep periods. For example, the rate of pumping of a medicine may be dependent on the density of the on periods (for example in FIG. 3E there are six 200 msec on periods during 10 sec for a density of 0.12).

A Medical Infusion Device

Figure 4:
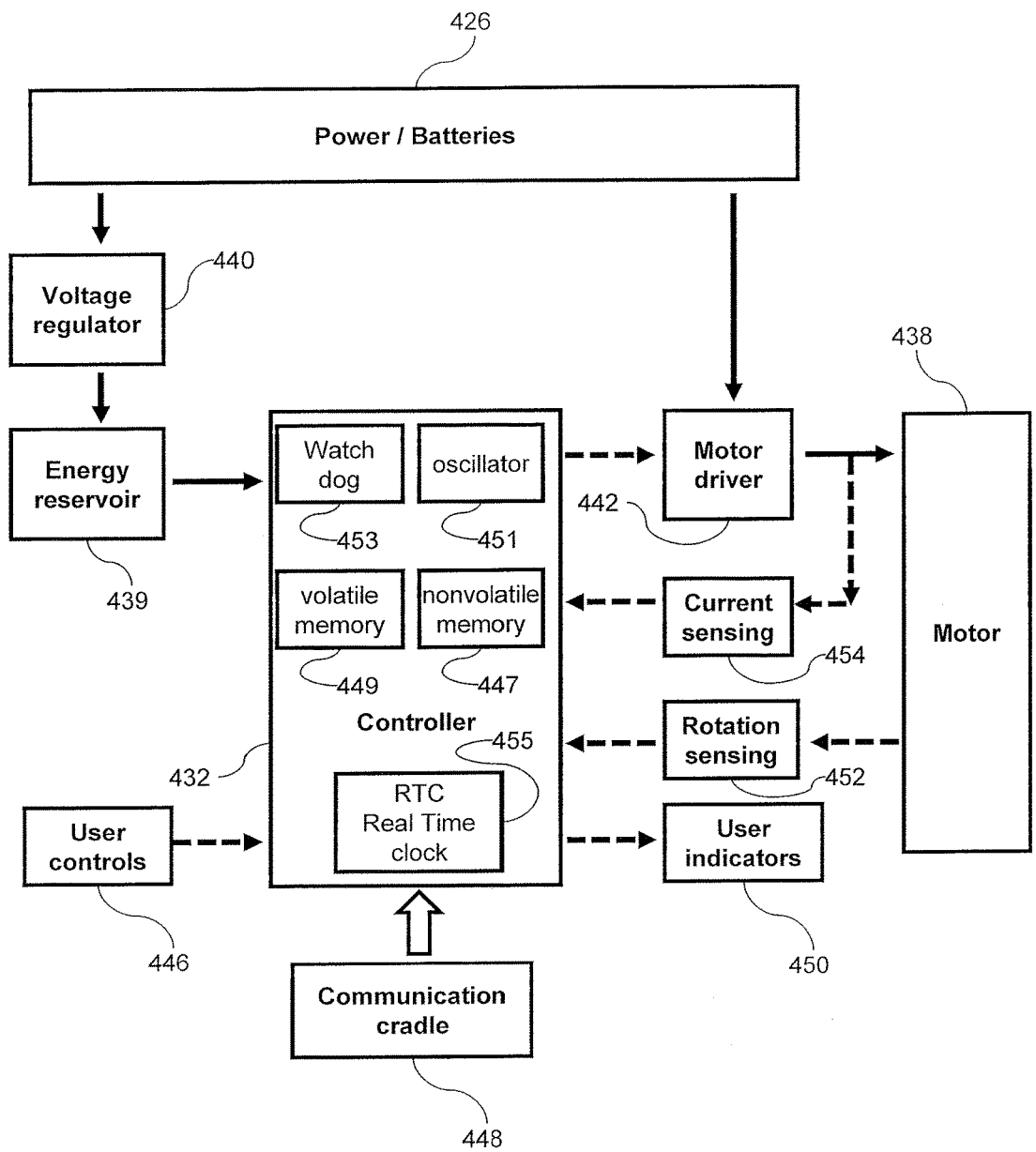
FIG. 4 is a block diagram of an infusion pump employing an exemplary embodiment of a system to provide power to two devices.

FIG. 4 is a block diagram illustration of an exemplary embodiment of a disposable portable medical infusion pump employing an exemplary embodiment of a power distribution system. The exemplary infusion system may be designed to be cheap, disposable, small and reliable. Optionally, the system may include a motor driven pump that requires a high current when it is running. Optionally, the system may include a controller which requires a stable input voltage. In some embodiments, a cheap, small, disposable power supply (for example three Ag2O batteries) may not be able to simultaneously supply both requirements directly.

In some embodiments, an infusion pump may be employed to inject a medication slowly over a long period of time. In this mode the controller may optionally run for a long time to keep track of injection progress. Optionally, the pump may be activated only for relatively short periods to supply incremental injections separated by large time intervals. For example, in such a case, a small increase in the power requirements of the controller while the motor is not running may cause a significant drain on the energy of the power supply.

In some embodiments it may be desirable to supply an energy reservoir for the controller. Optionally, it may be desirable that the reservoir be able to supply a dependable voltage to the controller even when the motor is running. Optionally, it may be desirable that the reservoir be able to supply a dependable voltage to the controller even when the voltage output of the battery drops below a reset threshold of the controller. Optionally, it may be desirable that the energy reservoir not significantly increase the power consumption of the controller when the motor is not running.

In the example of FIG. 4, optionally a motor 438 drives a pump (not shown) injecting a medication. The rate of injection is optionally controlled using a micro controller 432. Controller 432 may optionally include an oscillator 451 and a real time clock 455.

Figure 8:
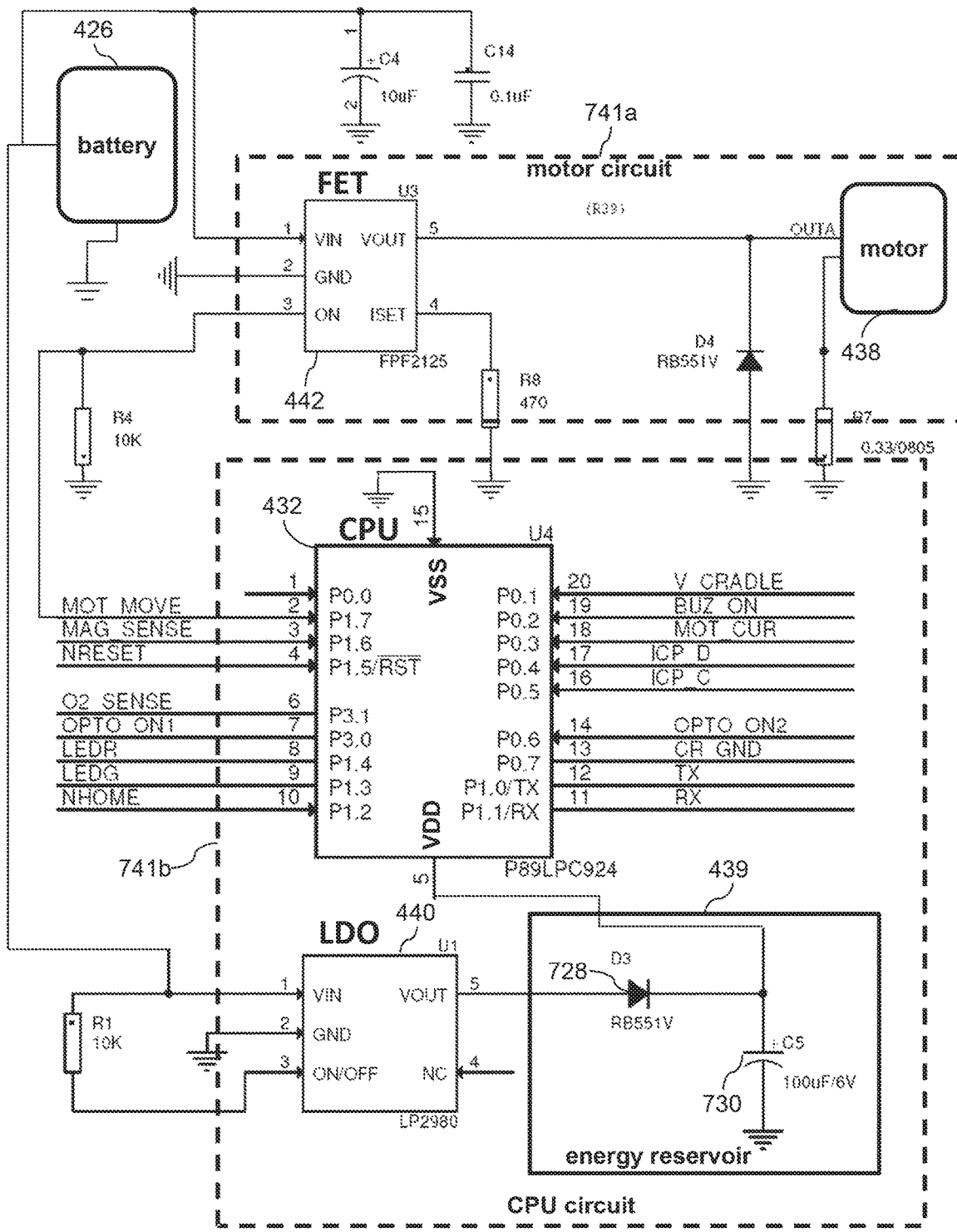
FIG. 8 is a detailed circuit diagram of an exemplary embodiment of a system to provide power to two devices.

In the exemplary embodiment of FIG. 4, controller 432 receives power from batteries 426 through voltage regulator 440 and energy reservoir 439. Energy reservoir 439 may optionally include a capacitor and/or a restrictor for example as illustrated in FIG. 8. Optionally, batteries 426 may also drive motor 438 via motor driver 442. Optionally, controller 432 controls motor 438 via motor driver 442. For example, motor driver 442 may include a FET and controller 432 may control the gate voltage to distribute the current to motor 438 in pulses.

In some embodiments, controller 432 may receive input signals indicating the status of the injector. For example: a current sensor 454 may report the current flowing to motor 438; a rotation sensor 452 may be used to track the rotations of the motor 438 and quantity of medicine injected.

In some embodiments, the medicine may be administered by repeated small doses. For example, the controller 432 may drive motor 438 for a 300 msec dosage period, measure the number of rotations, compute the quantity injected and determine a waiting time for next dosage in order to meet a stored injection rate and then wait and afterwards inject again for 300 msec. For some delivery rates, the waiting period between doses may for example range between 500 msec to 5 sec. For lower delivery rates the waiting period may range between 3 sec and 5 minutes. In the waiting period, the injector may be in a sleep mode. For example, in the sleep mode the controller 432 may remain active, measuring time until the next dosage and remembering the delivery parameters, but the motor 438 may be inactive. Optionally, the status indicators and/or the delivery parameters may be stored in a volatile memory 449. In some embodiments, it may be important that the controller 432 not reset. For example, resetting may cause loss of parameter values stored in a volatile memory. For example, resetting of the controller 432 may indicate a malfunction of the injector or cause a fault in the tracking of the injection, in some cases such a malfunction may for the patient to rush to the hospital or even endanger the patient's life.

In some embodiments, during the dosage period, the high current drawn by motor 438 may cause the voltage output of batteries 426 to drop below the reset threshold of controller 432. Optionally, reset of controller 432 may be avoided by commanding driver 442 to drive motor 438 with current pulses (for example in a manner similar to FIGS. 2 and 3). This may be achieved for example by controller 432 sending pulsed control signals to the FET of driver 442.

Alternatively or additionally, a boost regulator may be used to maintain controller input voltage greater than the voltage of the power source. Boost regulators may be inefficient and/or expensive in comparison to some embodiments of current redistribution. For example, in sleep mode the controller 432 may continue running from the battery output which may be greater than 3.0V while motor 438 is not be running. Under such conditions, a boost regulator inefficiently continues to draw power. In contrast, in some embodiments of a current distribution system, the distribution of the motor input may not be active during sleep mode. Optionally, under those conditions, the distribution system may not significantly increase the energy consumption of controller 432. In some embodiments (for example see FIG. 9), current redistribution (for example, using motor driver 442 to create cut off power to motor 438 thereby creating voltage spikes and using energy reservoir 939 to preserve a threshold voltage to controller 432) may be used for slow delivery rates (where, for example, energy consumption of the controller during sleep mode is important) and a boost regulator (for example regulator 940) may be used for high delivery rates (where, for example the sleep time is short and the inefficiency of having a boost regulator on the controller circuit may not be critical).

Optionally the infuser may include a communication cradle 448. Cradle 448 may be used, for example, to program a delivery rate for a drug. Optionally cradle 448 may also be used to adjust control parameters such as the length of a dosage period, the rate of current distribution. For example, for highly viscous drugs, motor 438 may draw more current while injecting the drug. Optionally for more viscous medicines, the length of distributed pulses may be reduced and/or the length of the dosage period may be reduced to avoid loss of voltage to controller 432.

In some embodiments, the system may include a non-volatile memory 447 (FIG. 4). The non-volatile memory 447 may store, for example, pre-programmed information programmed into the infuser using cradle 448. Optionally, the preprogramming may be done while being prepared for use, for example by the manufacturer and/or a doctor and/or a hospital employee and/or a pharmacist. Alternatively or additionally, the non-volatile memory 447 may include performance flags. Optionally flag values may be recording during operation and/or before shut down. When the infuser restarts, the flag values may be used to adjust parameters, for example, to improve operation and/or avoid repeated unintentional shut downs and/or to recognize a repeated malfunction.

In some embodiments the infuser may include dynamic adjustment of operating parameters. For example, the infuser may be able to adjust itself to adapt to conditions or performance parts that may not be known a-priori. For example, if the infuser is stored for a long time batteries 426 may not perform according to specifications. For example, if the infuser is used under cold conditions, the viscosity of the medicine may increase and the performance of batteries 426 may be poor. In such a case, during a dosage period, motor 438 may draw higher than expected current. In such a case, during a dosage period, the drop of voltage output of battery 426 may be more than expected. Optionally the infuser may include sensors (for example current sensor 454 and/or a voltage sensor [not shown]) to detect such changes in performance and dynamically adjust operating parameters (for example by shortening the dosage period or shortening the pulse length of the current distribution) to allow the infuser to continue operation and avoid malfunction.

In some embodiments, the performance characteristics of the infuser may be adjusted for secondary reasons. For example the rate of pulses may be adjusted to achieve a desired vibration (patients may feel more confident that the device is working if they hear a reassuring humming sound).

Controller 432 may optionally include a watch dog 453 to prevent uncontrolled injection upon failure of the controller. The injector may include optional user indicators 450 for example a malfunction alarm and/or an operating indicator LED. The injector may optionally include user controls 446 such as an activator button.

In some embodiments, the voltage distribution cut off period may have a length of, for example, between 2 and 50 msec. In some embodiments, the voltage distribution pulse to motor 438 may have a length of, for example, between 2 and 150 msec. In some embodiments, the duty cycle of the power distribution (pulses and cut offs) may range between 50% and 95%. In some embodiments, the pulse density modulation motor control may have a motor-on time ranging between 50 and 500 msec. In some embodiments, the pulse density modulation motor control may have a motor-off time ranging between 500 and 5000 msec. In some embodiments, the pulse density modulation motor control may have a duty cycle ranging between 2% and 20%.

Method of Dynamically Controlling a System Powering Two Devices

Figure 5:
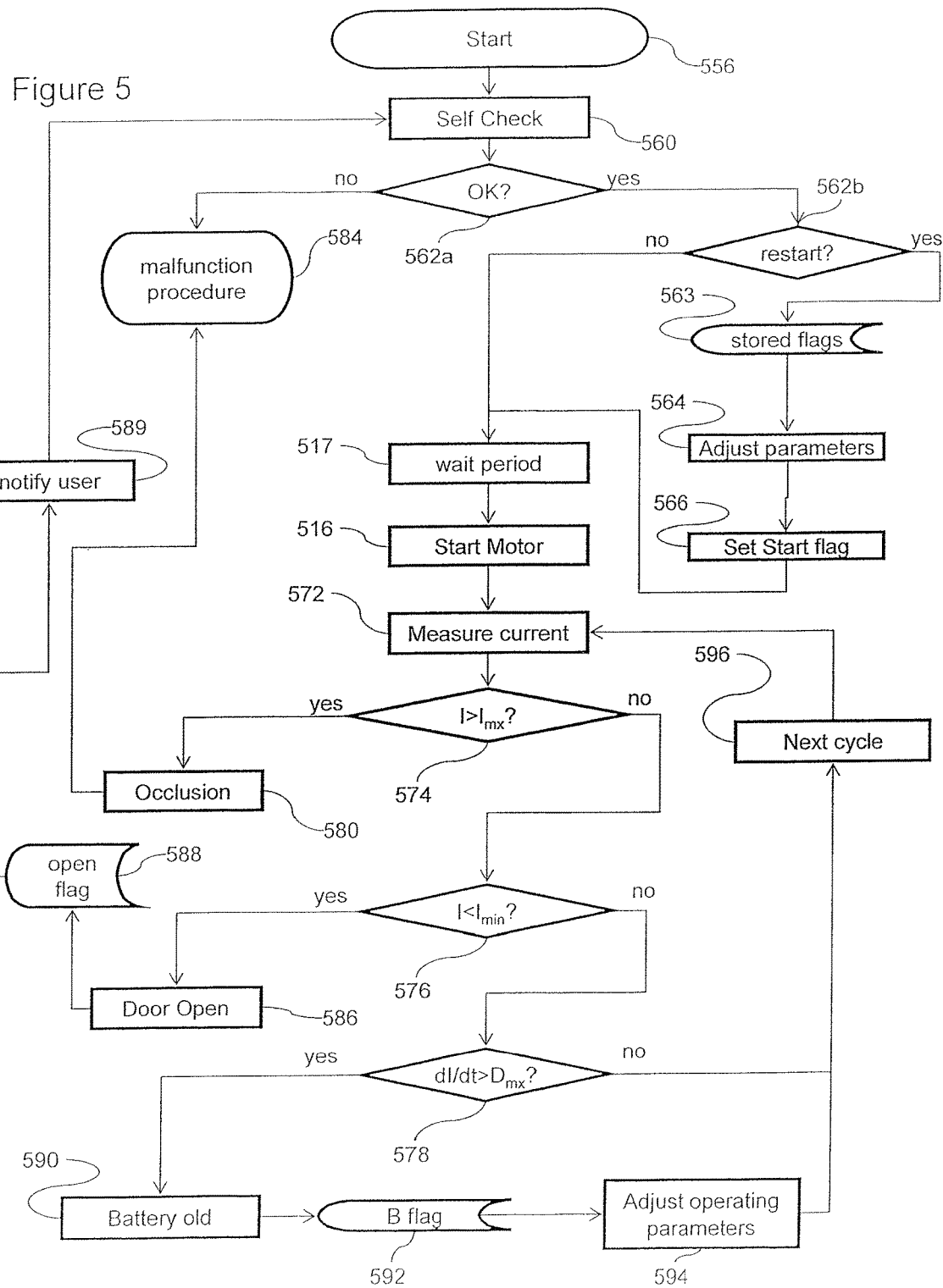
FIG. 5 is a flow chart illustration of dynamic adjustment of a system to provide power to two devices.

FIG. 5 is a flow chart illustration of a method for dynamically adjusting performance characteristics of a system for powering two devices with a single power source. Particularly in the example of FIG. 5, based on pre-stored parameters and/or on the output of various sensors, a controller adjusts parameters of various aspects of current distribution and/or motor control.

In some embodiments operating parameters may be adjusted at start up based on parameters programmed into a non-volatile memory. Alternatively or additionally, the non-volatile memory may include flags which are set during operation. For example if the controller resets during operation, flag values may optionally be read upon restart and used to adjust the system operating parameters.

In some embodiments, operating parameters may be adjusted dynamically during operation. For example, the parameters may be adjusted according to sensor outputs.

In the embodiment of FIG. 5, upon start up 556, the controller makes a self check 560. The self check may optionally include checking 562a various components for malfunctions. If there is a malfunction, a malfunction procedure 584 may optionally be initiated. For example, alarm may sound, an LED may be lit, and/or the infuser may shut down.

Alternatively or additionally, the self check may include checking 562b stored flags for a sign the injector had been activated previously and shut down and the current start up 556 is a restart. Optionally, stored flag values may be read 563 to determine the cause of the previous shut down. For example, the malfunction flags could indicate that there was a higher than expected current drain from the motor and/or that the battery performed worse than expected; this could be a sign of, for example, cold temperatures (that may increase medicine viscosity and decrease battery performance). According to the cause of the previous shut down, actions may optionally be taken to adjust 564 the operating parameters of the pump to avoid further malfunctions. Adjustments 564 may optionally include those listed above with respect to dynamic adjustment of operating parameters. Optionally, a restart flag may be set 566. In some embodiments, if the system fails again, the system will know that the system has been reset previously; for example this could be a sign of a serious malfunction.

In the exemplary embodiment of FIG. 5, parameters have been properly adjusted 564 and/or on a normal start, the injector may optionally wait 517 (for example until a prescribed injection time) and/or then start 516 the motor to inject the medicine.

In some embodiments, while the medicine is being injected, the current to the motor may be measured 572. Optionally, based on the measurement results operation of the pump may be dynamically adjusted.

For example, if the current is greater than a maximum threshold 574, there may be an occlusion 580. The controller may optionally perform malfunction procedure 584.

For example, if the current is less than a minimum threshold 576, the door of the pump may be open 586. The controller may optionally set a door open flag 588, notify the user 589, and/or restart the system from the self check 560.

For example, if the voltage to the controller is dropping at a rate greater than a maximum threshold 578, the battery may be old 590. The controller may optionally set a flag 592 and/or adjust 594 operating parameters before the next cycle 596.

Setting flag 592 may include for example saving performance and/or operational parameters to a non-volatile memory. Optionally, the stored parameters may include for example, the amount of medicine injected until now, the rate of injection, the measured voltage input to the CPU and/or the rate of change of voltage input to the CPU. There may optionally also be cumulative stored values, for example the amount of medicine injected may be stored in a nonvolatile memory periodically and/or when there is danger that the volatile memory will be reset (for example when the voltage to the CPU drops to near the reset threshold). If the CPU is reset, then upon restart 562b the stored injection volume may be used as the initial volume (thus treatment will be cumulative over restarts and the patient will not receive an overdose if the system shuts down and restarts and repeats the full dose).

Optionally, the stored parameters may be used by the controller for example in order to adjust the operating parameters on restart for example in order to avoid repeating the malfunction. Alternatively or additionally, the stored parameters may be used by technical and/or medical staff (for example avoid future malfunctions and/or to adjust the continued treatment of the patient).

Adjustments

Some example of adjustments 594 to operational parameters that may be made dependent on current measurements 572 and/or adjustments 594,564 may be made dependent on operational parameters read 563 from stored measurements. Adjustments may include, for example, one or more of:

- if the measured voltage to the CPU dipped too low, then the duty cycle of the current distribution may be reduced;
- if the voltage to the CPU during cut off times is greater than a cutoff voltage target level (e.g. well above the reset threshold of the CPU) but voltage is to the CPU is low at the end of the drive pulse to the motor, (in some embodiments this may mean that there is not enough storage capacity [for example capacitor 230 is too small]) then the drive pulse length may be made shorter;
- if the voltage during the cut off period does not rise to the target level than the cut off period may be lengthened;
- if the cut off period has been lengthened to a stored maximum cut-off period value, and the voltage still does not rise to the target level, then the motor-on time may be reduced;
- if the voltage is dropping too much over the long term, the density of the PDM may be reduced (in some embodiments, this may reduce the power output of the device [for example a pumping rate of an infuser]).

Measurements of Current and Voltage During the Distribution Cycle

Various embodiments and aspects of the present invention as delineated herein and as claimed in the claims section below find experimental support in the example of FIG. 6.

Figure 6:
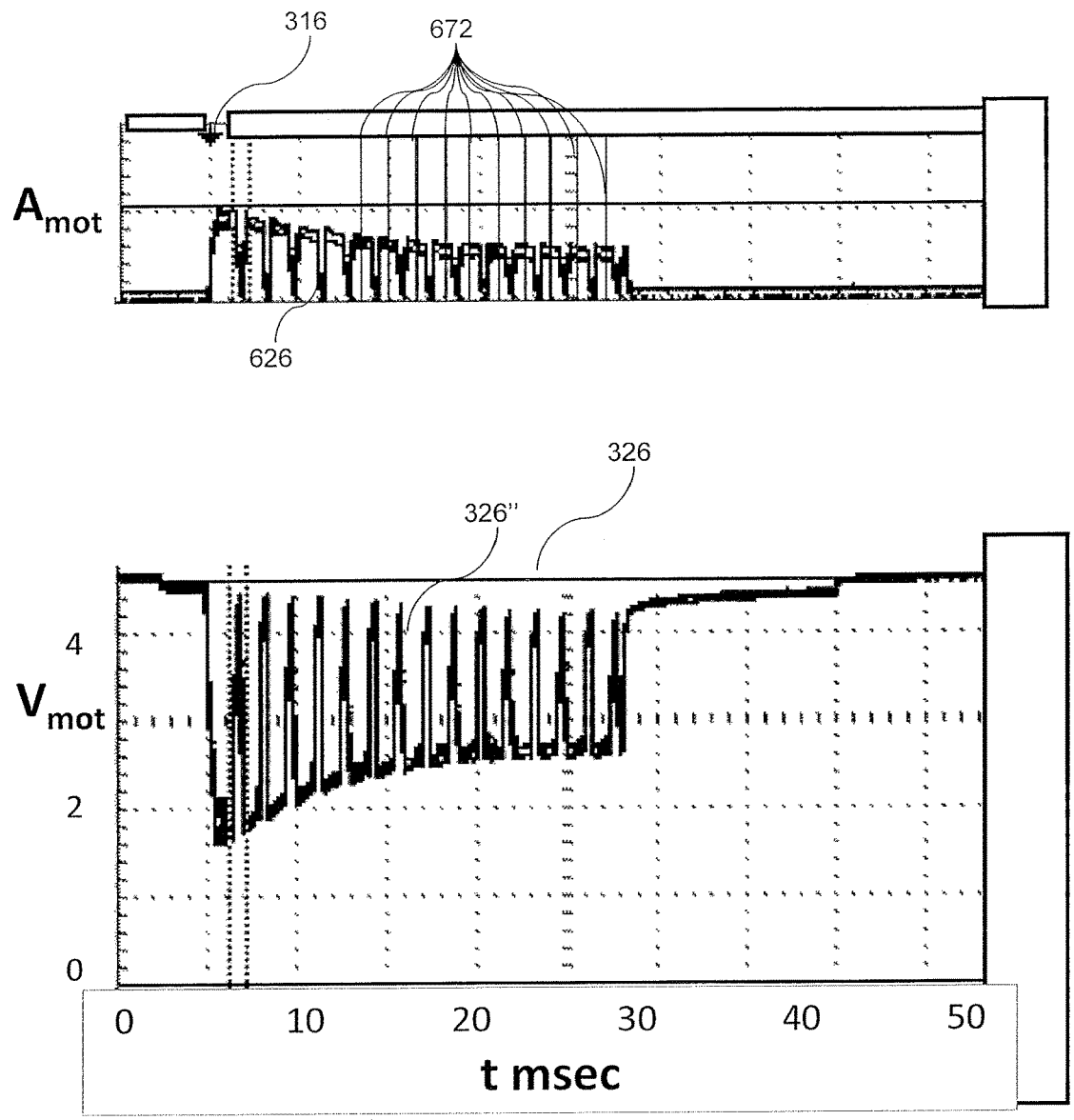
FIG. 6 is a graph showing experimental measurements of voltage over time, and current over time, and testing times in an exemplary embodiment of a method of providing power to multiple devices.

Reference is now made to the examples of FIG. 6, which together with the descriptions herein illustrate some embodiments of the invention in a non limiting fashion.

Some details of the experimental circuit used in FIG. 6 are shown in FIG. 7. FIG. 6 is a graphical illustration of experimental results for a system similar to that illustrated in FIG. 7. Experimental measurements of voltage 326" and current 626 input to the motor are shown.

Lines 672 illustrate measurement times for current at the motor. In the exemplary experiment, current was measured during the stable phase of the movement. Current was measured 10 msec after activation the motor when the voltage drain stabilized (for example, at start up a DC motor may draw a transient high current of 250% the working current of the motor). In the exemplary experiment, measurements were made near the middle of the motor driving pulse for ten consecutive pulses.

Circuit Details of a Exemplary Embodiment

FIG. 7 illustrates details of an exemplary embodiment wherein controller 432 controls switching and distribution of power to motor 438. Optionally, power is supplied from batteries 426 to controller 432 via a CPU circuit 741b. Optionally, power is supplied from batteries 426 to motor 438 via a motor circuit 741a.

In some embodiments, controller 432 sends control signals to a FET 734 to drive motor 438 and/or cut off power. Optionally, controller 432 may use driver 442 to turn motor 438 on or off, and/or to pump a medicine at a controlled rate. Alternatively or additionally, controller may use driver 442 to distribute power input to motor 438 in order to maintain sufficient voltage to controller 432.

In the exemplary embodiment of FIG. 7, voltage regulator 440 and energy reservoir 439 may optionally smooth voltage surges to supply a smooth voltage to controller 432. Optionally, reservoir 439 may include a restrictor 728 and a capacitor 730.

Optionally a controller interface is supplied by input cradle 448. Optionally, dynamic adjustment of operation may be based on inputs from rotation sensor 452 and/or current sensor 454. Alternatively or additionally, operation of the embodiment of FIG. 7 may be fixed. Alternatively or additionally, the embodiment of FIG. 7 may include some or none of sensors 452 and 454. Alternatively or additionally, the embodiment of FIG. 7 may include more sensors.

440 FIG. 8 includes even more circuit details of an exemplary embodiment of a voltage regulating system. Parts having similar function to parts of the embodiments of FIGS. 2, 4 and 7 are marked with the same numbers.

Device with an Optional Boost Regulator

Figure 9:
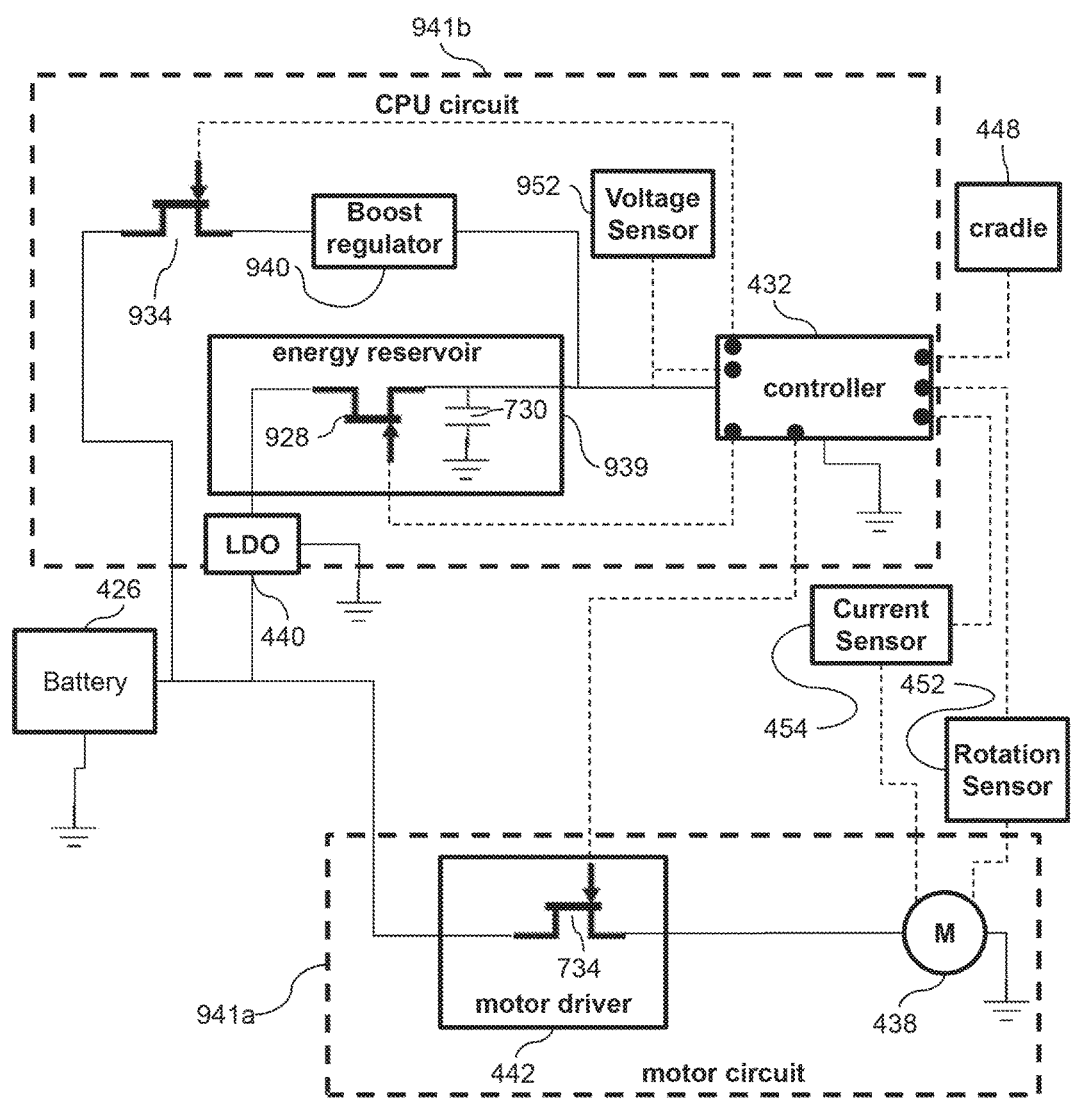
FIG. 9 is a circuit diagram of an exemplary embodiment of a system to provide power to two devices including an optional boost regulator.

FIG. 9 is a circuit diagram of an exemplary embodiment of a system for powering multiple devices. The exemplary embodiment of FIG. 9 includes an optional motor circuit 941a. Motor circuit 941b may, optionally supply pulsed and/or unpulsed power from batteries 426 to motor 438. The exemplary embodiment of FIG. 9 includes an optional CPU circuit 941b. CPU circuit 941b may, optionally supply power from batteries 426 to controller 432.

CPU circuit 941b may, optionally include an energy reservoir 939 and/or a boost regulator 940. Reservoir 939 may include an optional restrictor 928 including an active FET gate that may prevent high voltage power from draining from capacitor 730 to battery 426 and/or motor 438.

Boost regulator 940, may for example, maintain a voltage above a reset threshold for controller 432 even when the voltage output of battery 426 falls below the threshold voltage for an extended period.

Reservoir 939 may optionally maintain a voltage above a reset threshold for controller 432 when the voltage output of battery 426 falls below the threshold voltage for a short period. For example, when there is a low density PDM (for example as illustrated in FIG. 3A-E), FET 934 may be switched closed, and energy reservoir 939 may optionally maintain a desired threshold voltage to controller 432 by means of current distributing similar to that describe with respect to FIGS. 2, 3A-E and/or 4.

Optionally, active FET gate current restrictor 928 may prevent leakage of current from capacitor 230 to battery 426 and/or motor driver 442. For example, when voltage of battery 426 is low, controller 432 may close the gate of restrictor 928. For example, closing restrictor 928 may be in reaction to detecting low battery voltage via a voltage sensor across battery 426 (not shown). Alternatively or additionally, switching of restrictor 928 may be controlled by timing software. For example, the timing software may close restrictor 928 when FET 734 is open to supply high current to motor 438. Optionally controller 432 may then reopen restrictor 928 a few milliseconds after closing FET 734 (when it can be assumed that the voltage of battery 426 has risen above the cutoff threshold). Alternatively or additionally the embodiment of FIG. 9 may have include only some or none of the optional sensors 452, 454, 952.

In some embodiments, at some times, boost regulator 940 may be used to maintain voltage of controller 432. For example, boost regulator 940 may be used when voltage sensor 952 senses that voltage to controller 432 is dropping too low (for example, either voltage drops below a danger threshold and/or the voltage does not rise sufficiently when power to motor 438 is cut). Alternatively and/or additionally boost regulator 940 may be used when the pumping schedule is fast for example as illustrated in FIG. 10 and the accompanying explanation.

In some embodiments, when boost regulator 940 is in use, FET 934 is switched open and restrictor 928 is switched closed. Optionally boost regulator 940, may provide a high voltage input current to controller 432 even when the voltage of battery 426 falls below the threshold for an extended period. Optionally, when boost regulator 940 is in use, motor driver 442 may not be used for distributing power. For example, FET 734 may be switched on or off according to the needs of motor 438 and the required power output (for example, for a medical infuser, to control the pumping rate) without regard to the voltage input to controller 432.

High Rate Power Output

Figure 10:
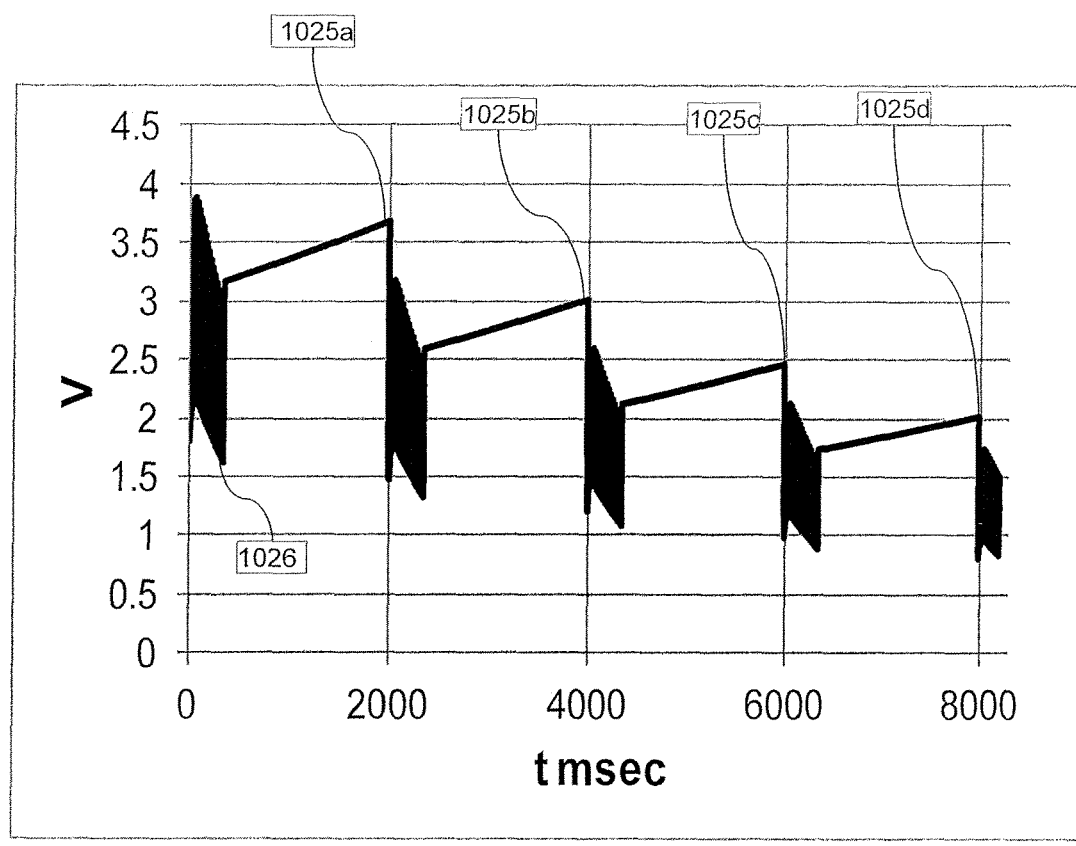
FIG. 10 is a large scale schematic diagram showing a few cycles of voltage over time to two devices powered by an exemplary embodiment of a method of providing power to multiple devices with a large duty cycle.

FIG. 10 illustrates voltage of time for example of driving a circuit at a high power output. In the exemplary embodiment of FIG. 10, the rest time of 750 msec between motor-on events of 350 msec is not enough time for the battery to regenerate to its full output. When there is not enough recovery time, battery voltage may, for example, decay over time. In the example of FIG. 10, the battery voltage may drop below a battery reset threshold (for example 2.4 V) and remain below the threshold for extended periods.

In the embodiment of FIG. 10, redistribution of current (as illustrated for example in FIGS. 1, 2, 3 and 4) may not be an efficient manner to maintain the voltage input of an integrated circuit above a reset threshold. Optionally, a boost regulator (for example boost regulator 940 of FIG. 9) may be used to maintain a high voltage potential for an integrated circuit (for example controller 432).

In FIG. 10, simulated battery output voltage 1026 is shown over time, for an exemplary embodiment. In the exemplary embodiment of FIG. 10, during motor-on events (in the example of FIG. 10 from 0-350 msec, from 2000-2350 msec, from 4000-4350 msec and from 6000-6350 msec) the batteries are drained and during the off events the batteries regenerate until they reach a peak 1025a, 1025b, 1025c, 1025d right before the next on event.

A possible disadvantage of use of boost regulator 940 is that the boost regulator 940 may consume power. For example, controller 432 may consume 0.5 mW of power. When power is supplied to controller 432 through boost regulator 940 the combination circuit may require 0.75 mW of power.

In cases where the device may continue to function for long periods of time (for example to slowly inject a drug), a small increase of power consumption of the CPU may be significant. The loss of energy due to use of a boost regulator may then be significant. Slow injection may, for example, use a small PDM duty cycle (for example as illustrated in FIG. 4A-E) wherein short cut periods may restore a battery output voltage above the CPU reset threshold. Optionally, in such a case, power distribution may be the preferred way of regulating voltage.

In the example of FIG. 10, during long periods where the battery output voltage remains below the CPU input threshold, (for example in FIG. 10 from 4000 msec until 5000 msec and from 6000 msec until 8000 msec) a boost regulator (for example boost regulator 940) may be used to maintain CPU input voltage. At other (for example from 0-4000 msec and from 5000-6000 msec) the boost regulator may be bypassed (for example by closing FET 934 and a CPU input threshold voltage may be maintained using a power distribution regulator system (for example, during motor-on events, using motor driver 442 to cut of power periodically to the motor and capacitor 230 to store energy and keep up the CPU voltage when the voltage output of the battery falls for short periods below the threshold).

General Notes

It is expected that during the life of a patent maturing from this application many relevant technologies will be developed and the scope of the various terms in the application are intended to include all such new technologies a priori.

As used herein the term "about" refers to ±5%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for increasing a voltage potential available to a controller sharing a power source with a motor, the method comprising:

producing transient high voltage surges in the output of the power source by repeatedly having a motor driver connected in series between the power source and the motor cut off power to the motor during predetermined spaced apart time periods, the motor driver being controlled by the controller;

storing, in an energy reservoir connected between the controller and the power source, energy during said surges;

releasing, by the energy reservoir, said stored energy to the controller while the motor is receiving power from the power source when a voltage output of said power source falls below a threshold voltage;

testing, by a voltage sensor, a voltage input to the controller;

receiving, by the controller, a result of the testing from the voltage sensor; and adjusting, by the controller, the cutting off of power by the motor driver to the motor based on the result of the testing in order to maintain the input voltage to the controller at or above the threshold voltage.

2. The method of claim 1, wherein the controller is comprised of at least one of an integrated circuit, a CPU, and a processor.

3. The method of claim 1, wherein the power source is comprised of at least one battery.

4. The method of claim 1, wherein the energy reservoir includes at least one of a diode or a transistor, the method further comprising:

preventing, by the diode or the transistor, leakage of said released energy away from the controller.

5. The method of claim 1, wherein said repeatedly cutting off of power to the motor has a period of between 5 and 50 milli-seconds.

6. The method of claim 1, wherein said repeatedly cutting off of power to the motor has a duty cycle of between 50% and 95%.

7. The method of claim 1, further comprising:
pumping a medicine with said motor; and
controlling a rate of said pumping with the controller.

8. The method of claim 7, wherein said controlling is adjusted for maintaining said threshold voltage to the controller accounting for an output limitation of the power source and a limit of said storage.

9. The method of claim 7, wherein said controlling is by pulse density modulation.

10. The method of claim 9, wherein said pulse density modulation has a pulse width of between 50 and 500 milli-seconds.

11. The method of claim 9, wherein said pulse density modulation has a duty cycle of between 2% and 20%.

12. A system for distributing power among a plurality components of a portable device, the system comprising:
a power source;
a motor;
a controller connected to the power source; and
a motor driver connected in series between the power source and the motor, the motor driver being controlled by the controller and being configured to:
supply to said motor, higher current pulses of power from said power source having sufficient energy to power said motor, and
at least partially cut off power to said motor between said pulses to produce voltage surges having sufficient energy to power said controller at a higher voltage potential than the potential of said higher current pulses; and
a voltage sensor configured to measure an input voltage to the controller, the controller being configured to receive output from the voltage sensor and to adjust the motor driver in response to the output of the voltage sensor to maintain the input voltage to the controller to be greater than a threshold value,
wherein power is supplied by the power source to the controller during and between the pulses.

13. The system of claim 12, further comprising:
an energy storage device connected between the power source and the controller, said energy storage device configured to store energy at a high voltage during said voltage surges, and
release said stored energy to the controller between said voltage surges.

14. The system of claim 12, wherein said motor has an inertia to keep operating during an inertial period and wherein said motor driver is configured to keep a length of a cut off period of power to the motor between said high current pulses less than a length of said inertial period.

15. The system of claim 12, wherein said adjusting includes at least one action selected from the group consisting of: lengthening a period of said cutting off of the power to the motor in response to a low value of said voltage input measurement, shortening a period between said cut off periods in response to a low value of said voltage input measurement, reducing a duty cycle of said motor in response to a low value of said voltage input measurement, lengthening a period of said cutting off of the power to the motor in response to a low value of said voltage output measurement, shortening a period between said cut off periods in response to a low value of said voltage output measurement, and reducing a duty cycle of said motor in response to a low value of said voltage output measurement.

* * * * *